US006228618B1

(12) United States Patent
Field (10) Patent No.: US 6,228,618 B1
(45) Date of Patent: *May 8, 2001

(54) METHODS FOR ENHANCED PRODUCTION OF TISSUE PLASMINOGEN ACTIVATOR IN CELL CULTURE USING ALKANOIC ACIDS OR SALTS THEREOF

(75) Inventor: Raymond Paul Field, Bourne End (GB)

(73) Assignee: Alusuisse Holdings A.G., Neuhausen am Rheinfall (CH)

( * ) Notice: Subject to any disclaimer, the term of this patent is extended or adjusted under 35 U.S.C. 154(b) by 0 days.

This patent is subject to a terminal disclaimer.

(21) Appl. No.: 08/955,526

(22) Filed: Oct. 22, 1997

Related U.S. Application Data (63) Continuation of application No. 08/358,552, filed on Dec. 14, 1994, now Pat. No. 5,681,718, which is a continuation of application No. 08/148,609, filed on Nov. 8, 1993, now abandoned, which is a continuation of application No. 07/879,133, filed on May 5, 1992, now abandoned, which is a continuation of application No. 07/663,050, filed on Feb. 27, 1991, now abandoned, which is a continuation of application No. 07/146,169, filed on Jan. 13, 1988, now abandoned.

(30) Foreign Application Priority Data

Mar. 14, 1986 (GB) .................................................. 8606386
Mar. 13, 1987 (WO) .................................. PCT/GB8700173

(51) Int. Cl.$^7$ .............................. C12N 15/09; C12N 5/12; A61K 35/14; C12P 21/04
(52) U.S. Cl. ........................ 435/69.2; 530/380; 435/70.2; 435/70.21; 435/172.1; 435/172.2; 435/172.3; 435/346
(58) Field of Search .................................. 435/69.2, 70.2, 435/70.21, 172.1, 172.2, 172.3, 346; 530/380

(56) References Cited

U.S. PATENT DOCUMENTS 4,469,790   9/1984   Yamane et al. .................... 435/172.1

FOREIGN PATENT DOCUMENTS 2122207   1/1994   (GB) .
57-74093   of 1982   (JP) .

OTHER PUBLICATIONS

*Catalogue of Cell Lines & Hybridomas*, 5$^{th}$ edition, pp. 85–86 (1985).
Adolf et al., "Spontaneous Production of α$^-$ and β—Interferon in Human Lymphoblastoid and Lymphoma Cell Lines", *Archives of Virology*, 72, pp. 169–178 (1982).
Adolf et al., "Interferon Production in Human Hematopoietic Cell Lines: Response to Chemicals and Characterization of Interferons Type 1 Replication", *Journal of Interferon Research*, vol. 2, No. 2, pp. 261–270 (1982).
Birch et al., "Bulk Production of Monoclonal Antibodies in Fermenters", *Trends in Biotechnology*, vol. 3, pp. 162–166 (1985).
Cho, Kyung Hea, "Effects of DNA Synthesis Inhibitors on the Induction of hCG Subunits and Alkaline Phosphatase in HeLa S$_3$ Cells", *Korean J. Biochem,* vol. 17, pp. 73–99 (1985).

(List continued on next page.)

Primary Examiner—Hankyel Park
(74) Attorney, Agent, or Firm—Venable; John W. Schneller (57) ABSTRACT

Methods for enhancing the production of tissue plasminogen activator (tPA) in cell culture are disclosed. The methods involve culturing tPA-producing cells in growth media supplemented with an alkanoic acid or salt thereof at a concentration which enhances tPA production. The most preferred methods utilize butyric acid or sodium butyrate at a concentration of between 0.5 mM and 2.5 mM.

8 Claims, 2 Drawing Sheets

○────○ No butyrate (control)
×·······× + 0.11mM butyrate
+────+ + 0.3mM butyrate
▲─ ─ ─▲ + 0.5mM butyrate
●────● + 1.0mM butyrate

OTHER PUBLICATIONS

Cleveland et al., "Routine Large–Scale Production of Monoclonal Antibodies in a Protein–Free Culture Medium", *Journal of Immunological Methods*, vol. 56, pp. 221–234 (1983).

Cox et al., "Effect of Media Composition on the Induction of Chorionic Gonadotropin by Sodium Butyrate in HeLa Cells", *In Vitro*, vol. 19, No. 1, pp. 1–6 (1983).

Ghosh et al., "Induction of Human Choriogonadotropin in HeLa–Cell Cultures by Aliphatic Monocarboxylates and Inhibitors of Deoxyribonucleic Acid Synthesis", *Biochem. Journal*, vol. 166, pp. 265–274 (1977).

Gorman et al., "Expression of Recombinant Plasmids in Mammalian Cells is Enhanced by Sodium Butyrate", *Nucleic Acids research*, 11, 21, pp. 7631–7648 (1983).

Kruh, Jacques, "Effects of Sodium Butyrate, a New Pharmacological Agent, on Cells in Culture", *J. of Molecular and Cellular Biochemistry*, vol. 42, pp. 65–82 (1982).

Le Gros et al., "The Effects of Sodium Butyrate on Lymphokine Production", *Lymphokine Research*, 4, 3 pp. 221–227 (1985).

Partington et al., "Human Globin Gene Transcription in Injected Xenopus Oocytes: Enhancement by Sodium Butyrate", *The EMBO Journal*, vol. 3, No. 12, pp. 2787–2792 (1984).

Williams et al., "Hybridomas Increase Antibody Production When Treated With Butyric Acid", *Hybridoma*, vol. 4, 1 p. 63 (1985).

Yuan et al., "Effect of Butyrate on the Expression of Microinjected or Transfected Genes", *Journal of Biological Chemistry*, vol. 260, No. 6, pp. 3778–3783 (1987).

Ning Huang et al., "Inhibition of IL–8 Gene Expression in CACO–2 Cells by Compounds Which Induce Histone Hyperacetylation", Cytokine, vol. 9, No. 1, pp. 27–36 (1997).

Effie Liakopoulou et al., "Stimulation of Fetal Hemoglobin Production by Short Chain Fatty Acids", Blood, vol. 86, No. 8, pp. 3227–3235 (1995).

Janine Arts et al., "Stimulation of Tissue–Type Plasminogen Activator Gene Expression by Sodium Butyrate and Trichostatin A in Human Endothelial Cells Involves Histone Acetylation", Biochem, J., pp. 171–176 (1995).

D.P. Palermo et al., "Production of Analytical Quantities of Recombinant Proteins in Chinese Hamster Ovary Cells Using Sodium Butyrate to Elevate Gene Expression", Journal of Biotechnology, 19, pp. 35–48 (1991).

Debra F. Nathan et al., "Increased Cell Surface EGF Receptor Expression During the Butyrate–Induced Differentiation of Human HCT–116 Colon Tumor Cell Clones[1]", Experimental Cell Research 190, pp. 76–85 (1990).

Cesar Roncero et al., "Hexanoate and Octanoate Inhibit Transcription of the Malic Enzyme and Fatty Acid Synthase Genes in Chick Embryo Hepatocytes in Culture", The Journal of Biological Chemistry, vol. 267, No. 21, pp. 14918–14927 (1992).

Akiyoshi Nishimura et al., "Short–Chain Fatty Acids Regulate IGF–Binding Protein Secretion by Intestinal Epithelial Cells", American Physiological Society, pp. E55–E63 (1998).

Babette Simon et al., "Transient Transcriptional Activation of Gastrin During Sodium Butyrate–Induced Differentiation of Islet Cells", Regulatory Peptides, pp. 143–148 (1997).

Teake Kooistra et al., "Butyrate Stimulates Tissue–Type Plasminogen–Activator Synthesis in Cultured Human Endothelial Cells", Biochem. J., pp. 605–612 (1987).

M.I. Cockett et al., "High Level Expression of Tissue Inhibitor of Metalloproteinases in Chinese Hamster Ovary Cells Using Glutamine Synthetase Gene Amplification", Bio/Technology, vol. 8, pp. 662–667 (1990).

METHODS FOR ENHANCED PRODUCTION OF TISSUE PLASMINOGEN ACTIVATOR IN CELL CULTURE USING ALKANOIC ACIDS OR SALTS THEREOF

This is a Continuation of application Ser. No. 08/358,552 filed Dec. 14, 1994 now U.S. Pat. No. 5,681,718, which is a continuation of application Ser. No. 08/148,609 filed Nov. 8, 1993, now abandoned, which is a continuation of application Ser. No. 07/879,133, filed May 5, 1992, now abandoned, which is a continuation of application Ser. No. 07/663,050, filed Feb. 27, 1991, now abandoned, which is a continuation of application Ser. No. 07/146,169, filed Jan. 13, 1988, now abandoned.

FIELD OF THE INVENTION

This invention relates to a process for the production of a protein by cell culture, where cells which produce the protein are cultured in the presence of a chemical agent which enhances production of the protein.

BACKGROUND TO THE INVENTION

Culturing cells for the commercial production of cellular products for diagnosis and therapy is a costly and time consuming process. The equipment required is expensive and research and development and production costs are high. In order to provide commercially viable processes it is desirable to use cell lines which produce large quantities of product.

Many naturally occurring cells do not produce large quantities of desired proteins, though may produce small quantities of the desired proteins constitutively, i.e. synthesise the proteins continuously. Other cell lines do not produce proteins of interest constitutively but it is well known that such cell lines may be induced to produce proteins of interest, i.e. these cell lines have the potential to produce particular proteins and when given an appropriate stimulus, will produce these proteins (Kruh, J., Mol. and Cell. Biol. 42, 65–82, 1982). Induction of protein production may be achieved by addition of a chemical compound, such as dimethylsulphoxide (DMSO) to the culture medium, or an infecting agent, such as Sendai virus to the cells.

A number of compounds are known which are able to act as 'inducing agents', 'enhancing agents' or 'stimulating agents' of protein production in cell lines. For the purposes of the present description the above terms have the following meanings based on the apparent effects which they cause. 'Inducing agent' refers to agents which apparently act to induce or initiate protein production. 'Enhancing agent' refers to agents which apparently act to increase, but may not initiate or induce, protein production. Enhancing agents may be added to the cell culture at or shortly after induction cell lines or at any time for cell lines which constitutively produce desired proteins. 'Stimulating agent' refers to agents which are added to cultures of inducible cell lines, usually after the cells have reached a desired cell density but before induction of protein production, and apparently act as part of a 'trigger' mechanism for subsequent induction of protein production, by an inducing agent.

The choice of agent, whether it be an inducing agent, enhancing agent or stimulating agent, depends on such factors as cell type, final concentration of the added agent in the medium, time of addition, period of exposure to the agent and toxicity. Many additives have been used, such as DMSO, urea derivatives and alkanoic acids or salts. From amongst such additives, sodium butyrate has been the subject of study in recent years. This compound has been added, at millimolar concentrations, to cultures of a variety of naturally occurring and selected cell lines and has been shown to produce many morphological and biochemical modifications in a reversible manner (Kruh, J., loc. cit.). At the molecular level, butyrate is believed to cause hyperacetylations of histones by inhibiting histone deacetylase. Generally, butyrate appears to modify gene expression and in almost all cases its addition to cells in culture appears to arrest cell growth.

For example, sodium butyrate (1 mM) has been used to induce human choriogonadotropin synthesis in HeLa-cell cultures (Ghosh et al, Biochem. J. (1977) 166 265–274; and Cox & McClure, In Vitro, Vol. 19, No. 1, January 1983, 1–6); though in both cases butyrate treatment inhibited cell growth. Also UK patent specification 2122207A describes the use of butyrate as a stimulating agent prior to induction of interferon synthesis with Sendai virus in a lymphoblastoid cell line. However, UK 2122207A further teaches, in the case of the particular cell line described, that butyrate could not be used as an enhancing agent of interferon synthesis if added at or shortly after induction.

In addition to cell lines which require induction to produce proteins of interest in large quantities, there are other cell lines available which are capable of producing desired proteins constitutively, i.e. without the need to use agents to induce protein synthesis (Trends in Biotech. 3. No. 12 (1985), J. Immuno. Meth. 56, 221–234 1983). Such cell lines include genetically manipulated cell lines and hybridoma cell lines. By use of selected genetically manipulated and hybridoma cell lines it has become possible to manufacture large quantities of 'rare' proteins, without the need to use inducing agents.

The effect of adding butyrate, a recognised inducer of protein production in several mammalian cell lines, has been studied for cultures of certain genetically manipulated cell lines. For example, cultures of Syrian hamster cells which were microinjected or transfected with a plasmid containing the entire SV40 genome and a gene coding for herpes simplex virus thymidine kinase (HSV-TK) (Yuan et al J. Biol. Chem. 260, 3778–3783, 1985) have been treated with butyrate. Butyrate was added to the cell culture and butyrate concentration was maintained throughout the culture period. The level of expression of SV40 was measured by determination of the amount of SV40 T antigen produced, and the level of expression of HSV-TK was measured by the incorporation of tritiated thymidine. Yuan et al reported that butyrate at concentrations ranging from 1 mM to 5 mM inhibited the expression of both genes as compared with control values.

Further, other workers (Gorman, C. M. et al. Nucleic Acids Research. 11, 7631–7648, 1983) have studied the effects of sodium butyrate on DNA-mediated gene transfer in an effort to investigate interrelationships between chromatin structure and expression of recombinant plasmids. In both transient expression and stable transformation experiments cells were treated with butyrate immediately following transfection with plasmids containing foreign DNA. In the case of stable transformants cells were also subjected to a second butyrate treatment five weeks after the initial butyrate treatment which immediately followed transfection. Their results indicate that butyrate affects the early stages of gene activity at least at two levels: increasing both the proportion of cells which are able to express foreign DNA and the level of enhancer dependent transcription. Further the results of their experiments with stable transformants indicate that expression of integrated recombinant plasmid genes is reinducible by subsequent butyrate treatment when the cells had been initially treated with butyrate immediately following DNA uptake. No appreciable induction of foreign gene expression was observed with cells which had not been subjected to an initial butyrate treatment immediately following transfection. These results suggest that the initial butyrate treatment predisposes expression of the integrated foreign DNA to subsequent butyrate induction.

In summary butyrate has been added to cultures of a number of natural and genetically manipulated call lines, generally appearing to initiate or inhibit gene expression and arrest cell growth. In the case of genetically manipulated cells, prolonged butyrate treatment appears to inhibit expression of foreign genes (Yuan et al, loc. cit.). In the specific instance when cells had been treated with butyrate immediately following transfection, subsequent butyrate treatment appears to reinduce expression of the foreign genes (Gorman et al, loc. cit.). The effect of butyrate treatment on the growth and immunoglobulin production of hybridoma cell cultures does not appear to have been investigated.

We have now found that chemical agents, such as butyrate, may be used to enhance protein production in cultures of genetically manipulated and hybridoma cell lines which are constitutive producers of the protein, provided that appropriate concentrations of the agent are added to the culture medium. We have found, in the case of genetically manipulated cells, that initial treatment with an agent, such as butyrate, immediately following transfection is not required to obtain enhanced levels of protein production on treatment of the cells with the agent during culturing. In particular we have found, contrary to expectation, that agents such as butyrate may be added to cultures of hybridoma cells at concentrations which enhance protein production but do not substantially decrease cell growth. Moreover, we have found that, although more elevated levels of agents such as butyrate may inhibit growth of genetically manipulated and hybridoma cells, concentrations of agent may be used which enhance protein production but do not significantly reduce cell viability.

SUMMARY OF THE INVENTION

Accordingly, in a first aspect the present invention provides a process for the production of a protein which comprises culturing genetically manipulated or hybridoma cells which constitutively produce said protein in the presence of an agent which enhances protein production wherein the agent is present at a concentration at which production of said protein is enhanced but at which cell growth rate is not substantially decreased.

In a further aspect of the invention we provide a process for obtaining a protein by cell culture which comprises the steps of (1) culturing genetically manipulated or hybridoma cells which constitutively produce said protein in the presence of an agent which enhances protein production, wherein the agent is present at a concentration at which production of said protein is enhanced but at which cell growth rate is not substantially decreased (2) continuing said culture until said protein accumulates and optionally (3) isolating said protein.

In the present invention, cells which produce a protein constitutively are to be understood to be those cells which do not need to be induced to produce the protein.

The term "genetically manipulated cells" refers to cells which have been transfected or transformed with exogenous DNA coding for a desired protein to provide transformed cells which constitutively produce the desired protein. Such genetically manipulated cells include cells in which the exogenous DNA is maintained episomally within, or integrated into the genome of, the transformed cells. Suitable host cells for preparation of such genetically manipulated cells include all host cell types though typically comprise eucaryotic cells including yeast cells or preferably animal cells, e.g. mammalian cells.

The term 'hybridoma cells' generally refers to hybrid cells produced by fusion of antibody producing cells, e.g. B-lymphocytes, with suitable myeloma cells. However, in the present description, the term 'hybridoma cells' also includes 'immortalised' antibody-producing cells produced by treatment of antibody-producing cells, e.g. B-lymphocytes, with transforming agents, such as Epstein-Barr virus (EBV). The 'hybridoma cells' of the present invention are typically of animal origin, for instance mouse or rat hybridoma cells or hybridoma cells derived from human cells.

The protein produced in the process of the invention may comprise a recombinant protein; for example, a useful and/or therapeutic eucaryotic protein such as a hormone, e.g. growth hormone such as human growth hormone, an enzyme, for example tissue plasminogen activator, an enzyme inhibitor, for example tissue inhibitor of metalloproteinase or a lymphokine. Also the protein may comprise an immunoglobulin molecule, in particular when the cells are hybridoma cells. Such immunoglobulin molecules include natural antibody molecules or analogues thereof or parts of either of these e.g. natural or analogue FAb fragments. The process of the invention is particularly useful for the production of immunoglobulins from hybridoma cells.

The agent used to enhance protein production in the process of the invention (hereinafter referred to as the enhancing agent) typically comprises a chemical agent provided that it may be used at a concentration which increases protein production but which does not substantially decrease cell growth rate.

Preferably the enhancing agent may be selected from the group comprising straight or branched chain, saturated or unsaturated fatty acids, particularly alkanoic acids, and salts thereof. In particular the enhancing agent comprises a straight chain alkanoic acid or salt thereof of between one and ten carbon atoms in length, more preferably of from three to six carbon atoms in length. Without prejudice to the above it appears that compounds having even numbers of carbon atoms are more potent than compounds having odd numbers of carbon atoms. Most preferably, the enhancing agent is butyric acid or a salt thereof, in particular an alkali metal salt, and is especially a butyrate salt, e.g. sodium butyrate.

The enhancing agent may be present in the culture medium at a concentration of between 0.01 mM and 500 mM, preferably between 0.1 mM and 200 mM and most preferably between 0.2 mM and 10 mM. In the case of transformed cell lines and other mammalian cell lines, the most preferred concentration range lies between 1 mM and 10 mM. In the case of hybridoma cell lines the concentration range is preferably between 0.1 mM and 0.9 mM, more preferably between 0.3 mM and 0.7 mM and most preferably is between 0.4 mM and 0.6 mM. It will be appreciated, however, that the concentration of the enhancing agent employed may be varied having regard to the particular cell line being cultured. The most appropriate concentration of enhancing agent for any particular cell line may need to be determined by appropriate small scale tests beforehand in accordance with conventional practice.

According to a preferred aspect of the invention we provide a process for obtaining a protein by culture of hybridoma cells which comprises the steps of (1) culturing hybridoma cells which constitutively produce said protein in the presence of an agent which enhances protein production wherein the agent is present at a concentration at which production of said protein is enhanced but at which cell growth rate is not substantially decreased, (2) continuing the culture until said protein accumulates and optionally (3) isolating said protein.

In this preferred aspect, the hybridoma cells are preferably mouse or rat hybridoma cells.

The protein produced by the process is preferably an immunoglobulin.

The enhancing agent is preferably an alkanoic acid or a salt thereof, preferably a straight chain $C_{2-10}$, especially a $C_{3-6}$, alkanoic acid or a salt thereof and in particular is butyric acid or a salt thereof, especially an alkali metal salt such as sodium butyrate. The enhancing agent is preferably present in the culture medium in the concentration range between 0.1 mM and 0.9 mM, more preferably between 0.3 mM and 0.7 mM, particularly between 0.4 mM and 0.6 mM.

Any suitable culture procedure and culture medium may be used to culture the cells in the process of the invention. Suitable culture procedures are well known and understood by workers in the cell culture art—see, for example, J. Immun. Meth. 56, 221–234 (1983). Both serum supplemented and serum free media may be used. Batch and continuous fermentation procedures, suspension and to adherent, e.g. microcarrier culture methods and stirred tank and airlift fermenters may be used as appropriate having regard to cell type.

In the process according to the invention, the enhancing agent may be added to the culture medium at, before or after addition of the cells to the culture medium. If desired more than one addition of enhancing agent may be employed. Thus, for example, it may be desirable to add the enhancing agent at the beginning of the culture and then to add more enhancing agent as the culture proceeds, providing of course that the addition is closely controlled such that the concentration of enhancing agent does not go beyond that which is likely to reduce cell growth rate.

The production of the protein during the culture may be monitored by general assay techniques such as enzyme linked immunosorbent assay or immunoradiometric assay adapted for the particular protein in question.

The desired protein may, if required, be isolated from the cell culture by conventional separation techniques. Thus, for example, protein in the culture medium may be separated from cells by centrifugation, the supernatant containing the protein being collected after concentration, for example by ultrafiltration. The protein to obtained may be further purified, if desired, using conventional protein purification methods. Where the desired protein is not secreted into the culture medium during the culture it may obtained by rupture of the cells, then subsequent processing as just described.

The enhancing agents described above may also be used to increase protein production in cells which have stopped growing exponentially and are in stationary or decline phases of growth. This is particularly advantageous when the desired protein is only produced by the cell when it is in these last two phases.

Thus in another aspect the invention provides a process for the production of a protein which comprises maintaining genetically manipulated or hybridoma cells which constitutively produce said protein in culture in the presence of an agent which enhances protein production wherein the agent is present at a concentration at which production of said protein is enhanced but which does not significantly reduce cell viability (e.g. is substantially non-toxic to the cells).

The cells, enhancing agents and culture procedures used in this aspect of the invention include those described in detail above. The culture medium used preferably comprises a medium which supports cell viability but which does not encourage cell growth. Such media include so called maintenance media and as such may not contain essential growth factors such as transferrin, insulin, albumin and the like.

Typically in this aspect of the invention, the cells are grown in culture to provide the levels of biomass required for efficient protein production. An enhancing agent may be included in the growth medium if desired but in some circumstances, however, it may be desirable to grow the cells in the absence of an enhancing agent, for instance, when production of the protein has a deleterious effect on the cells. Thus cells may be grown to densities at or approaching maximum cell density in the case of suspension cultures, or to or approaching confluence in the case of adherent cell lines, at which stage they may be transferred to a maintenance medium and the enhancing agent added at a concentration which enhances protein production but which does not significantly reduce cell viability. In general, suitable concentrations of enhancing agent will be those described above and may be for example between 0.1 mM and 500 mM, more preferably between 0.1 mM and 200 mM, most preferably between 1 mM and 5 mM, the exact concentration depending on the cell type used.

In yet another aspect, the invention provides a process for the production of a protein which comprises a first stage in which genetically manipulated or hybridoma cells which constitutively produce said protein are grown in growth medium until a predetermined cell density has been obtained followed by a second state in which said cells are maintained in the presence of an agent which enhances protein production wherein said agent is present at a concentration at which production of said protein is enhanced but at which cell growth is inhibited without significantly reducing cell viability.

This embodiment of the invention is particularly applicable to genetically manipulated cell lines which are intermediate or low producers of a desired protein, making it possible to substantially increase protein production by use of the enhancing agent at an appropriate concentration.

The growth medium may contain an agent which enhances production of the protein though preferably does not. The predetermined cell density to which the cells are grown in the first stage is preferably a cell density suitable for efficient protein production such as a density approaching maximum cell density for the culture or approaching confluence. The concentration of enhancing agent used in the second stage will generally be as described previously but in particular will be such to arrest cell growth, prolong the period of cell viability and yield an increased level of overall protein production.

An advantage of adding a chemical agent such as, for example, sodium butyrate to the culture system as outlined above is that protein production can be substantially increased for a very small outlay in expenditure, and little if any alteration to culturing techniques. A further advantage is that the cells are constitutive producers of the desired proteins and do not require induction to produce large quantities of desired proteins, and hence the production protocols remain simple, the addition of butyrate within an appropriate concentration range dependent on cell line serving to potentiate protein production.

BRIEF DESCRIPTION OF THE DRAWINGS

The invention is now described by way of illustration only in the following examples which refer to the accompanying diagrams in which.

DESCRIPTION OF SPECIFIC EMBODIMENTS

EXAMPLE 1

Effect of Sodium Butyrate on Hybridoma Call Growth and Antibody Production

The IgM secreting mouse hybridoma cell line NB1/19 was grown in suspension culture in Dulbeccos Modified Eagles Minimum (DMEM) serum-free medium containing albumin, insulin, transferrin, gentamycin and other additives as required to cultivate cells in suspension culture. The NB1/19 cell line produces a mouse monoclonal antibody having specificity for an antigenic determinant of human B-type blood cells. The preparation of this cell line is described in detail in the specification of British Patent GB 2097425B. It will be appreciated, however, that other hybridoma cell lines may be used in place of this particular cell line as appropriate in this and other examples.

The cells were grown to a viable cell density of $1.0-1.5 \times 10^6$ cells/ml. Viable cell density was determined by counting the number of cells which exclude trypan blue, a staining agent. A sample of the suspension culture was diluted in a serum-free medium to a density of about $1.3 \times 10^5$ cells/ml. Aliquots of 50 ml in volume were dispensed into shake flasks and sodium butyrate added at concentrations of 0.1 mM, 0.3 mM, 0.5 mM and 1.0 mM.

The shake flasks were gassed with 5% $CO_2$-95% air, and sealed and incubated with shaking at 37° C. for up to 207 hours. (Table 1). Samples (1.0 ml) were removed from the culture by pipette. 100 μl was used to determine viable cell count and the remainder centrifuged at 300×g for five minutes. Supernatants were stored at −20° C. prior to antibody determination by enzyme linked immunosorbent assay (ELISA).

Figure 1:
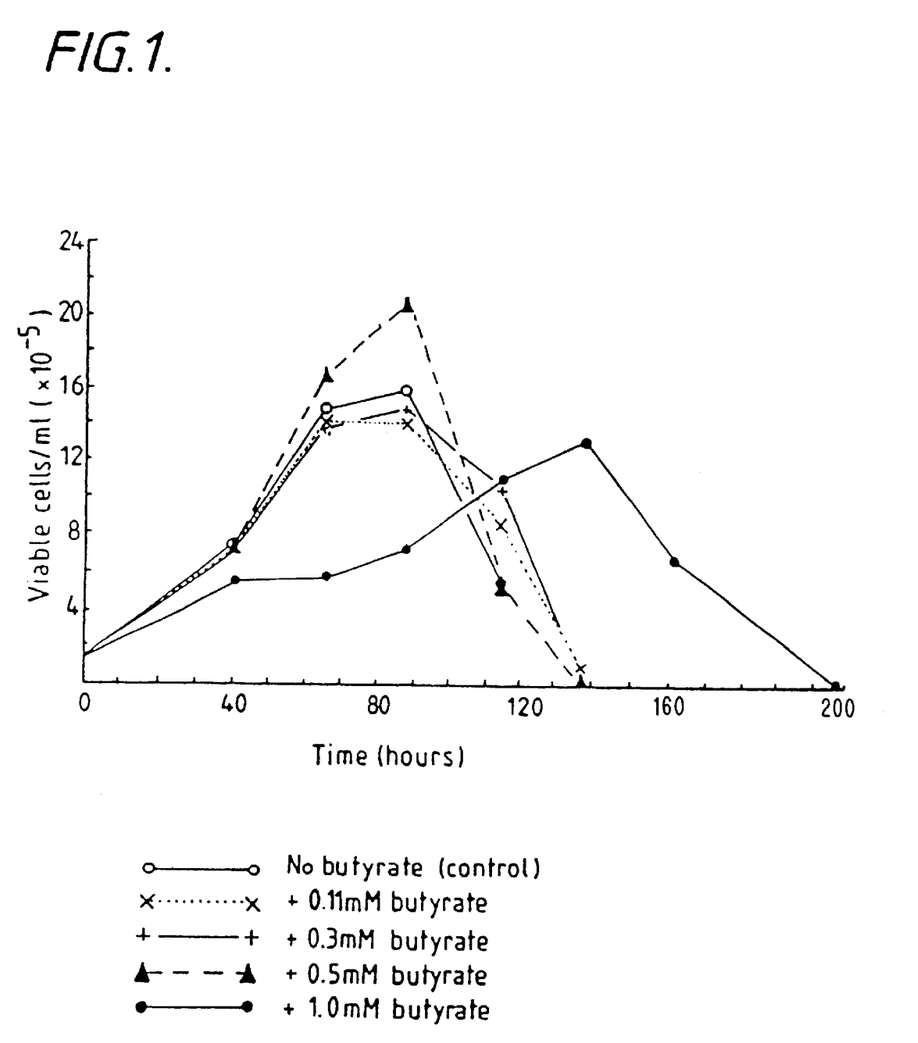
FIG. 1 is a graph showing the effect of butyrate or hybridoma cell proliferation in serum free medium.

FIG. 1 and Table 1 show the effects of varying butyrate concentration on hybridoma cell growth and antibody production, respectively.

TABLE 1

A. Effect of butyrate on the antibody production profile in serum-free medium

| Concentration of sodium butyrate (mM) | Time (hours) | | | |
|---|---|---|---|---|
| | 41 | 87 | 137 | 207 |
| 0 | 33 | 71 | 129 | ND |
| 0.1 | 34 | 90 | 128 | ND |
| 0.3 | 41 | 114 | 147 | ND |
| 0.5 | 50 | 173 | 173 | ND |
| 1.0 | 39 | ND | 180 | 256 |

(ND = not done)
antibody concentration (μg/ml)

B. Effect of butyrate on specific rate of antibody production in serum-free medium

| Concentration of sodium butyrate (mM) | Average specific rate of antibody production (μg/$10^6$ cells/day) |
|---|---|
| 0 | 26 |
| 0.1 | 26 |
| 0.3 | 26 |
| 0.5 | 31 |
| 1.0 | 52 |

EXAMPLE 2

Butyrate Enhanced Antibody Production in Hybridoma Calls Cultured in Serum Supplemented Medium The protocol for this experiment is similar to that outlined in Example 1, except that the cells were cultured in Dulbeccos Modified Eagles Minimum medium supplemented with 10% foetal calf serum.

Table 2 shows the effects on antibody production of adding sodium butyrate.

TABLE 2

Effect of butyrate on antibody production in serum supplemented medium

| Concentration of sodium butyrate (mM) | Maximum antibody concentration (μg/ml) | Average specific rate of antibody production (μg/$10^6$ cells/day) |
|---|---|---|
| 0 | 32 | 25 |
| 0.5 | 54 | 39 |
| 0.75 | 55 | 69 |

EXAMPLE 3

Butyrate Enhanced Antibody Production in Hybridoma Calls Cultured in Airlift Fermenters NB2/19 hybridoma calls were-cultured in suspension in airlift fermenters (Birch et al Trends in Biotech, Vol. 3 No.7, pp 162–166), (5 liters), in DMEM serum-free medium containing glutamine, transferrin, albumin, insulin and the like. Hybridoma cells were innoculated into the fermenter at a cell density of $1 \times 10^5$ cells/ml.

Sodium Butyrate was added to the fermenters at a concentration of 0.5 mM at the time of inoculation of the hybridoma cells into the fermenter.

Controls were not treated with sodium butyrate. Samples were periodically taken as described in Example 1.

Figure 2:
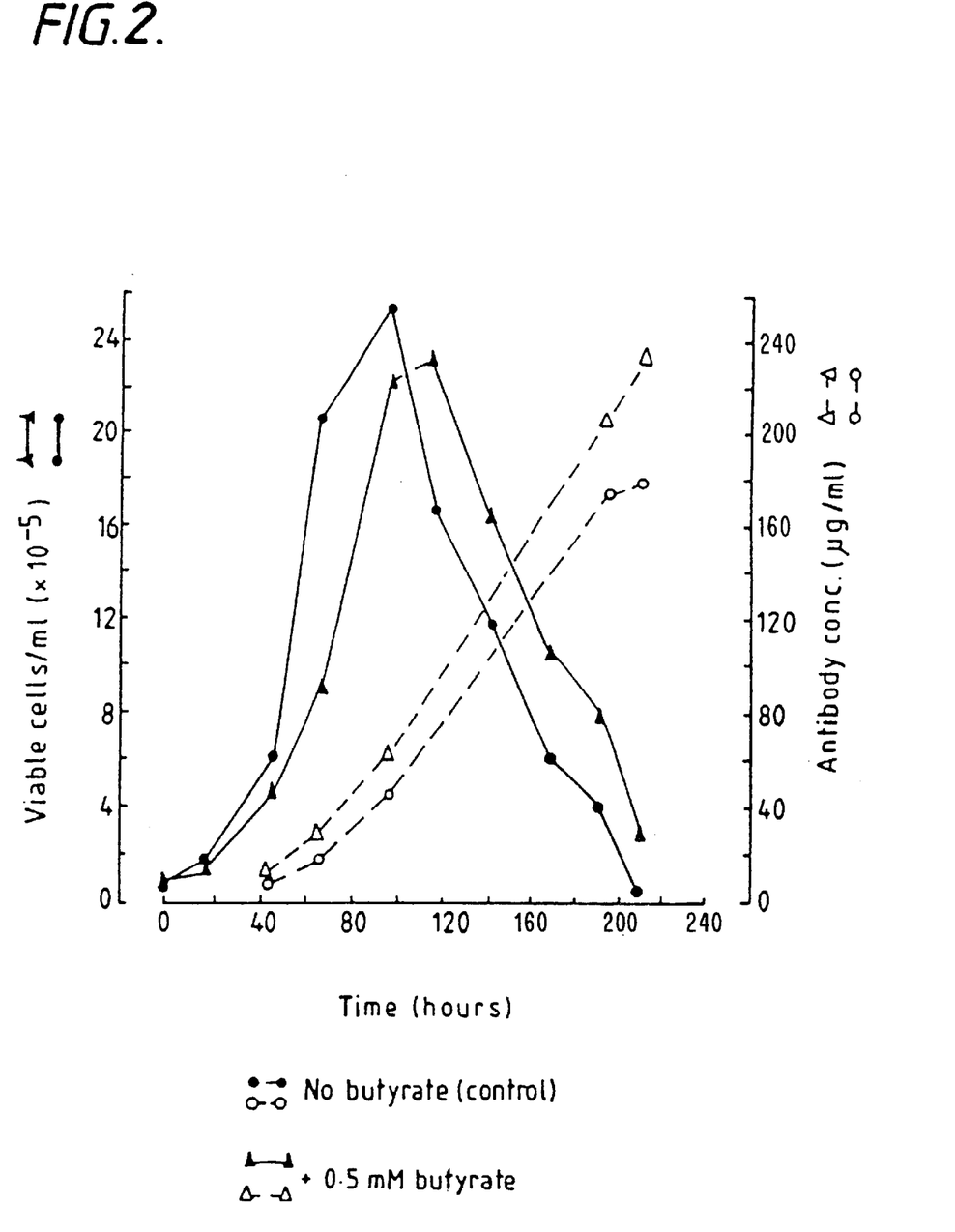
FIG. 2 is a graph showing the effect of butyrate on hybridoma cell proliferation and antibody production in an airlift fermenter.

The effects of butyrate on cell growth and antibody production are shown in FIG. 2.

EXAMPLE 4

Enhanced Production of Recombinant Human Growth Hormone in Mammalian Cells using Sodium Butyrate The molecular biology of adherent CBMG human growth hormone producing cells has been described (G. N. Pavlakis et al PNAS (USA) Vol. 80 pp 397–401 (1983)).

CBMG cells were inoculated into tissue culture flasks at a density of $0.7 \times 10^5$ cells/cm$^2$ in Dulbeccos Modified Eagles Minimum (DMEM) supplemented with 10% foetal calf serum.

After the cells in culture had grown to confluency, the DMEM serum supplemented medium was replaced by serum-free DMEM maintenance medium. Sodium butyrate was added at 1 mM and 5 mM after transferring the cells from serum supplemented medium to maintenance medium. Levels of human growth hormone in the culture supernatant were measured after 48 hours by immunoradiometric assay. The results are shown in Table 3.

TABLE 3

Effect of sodium butyrate on production of human growth hormone by CBMG cells

| Concentration of sodium butyrate (mM) | Concentration of hGH in supernatant (arbitrary units/48 hours) |
| --- | --- |
| 0 | 1.0 |
| 1 | 1.1 |
| 5 | 2.3 |

EXAMPLE 5

Effect of Sodium Butyrate on a Variety of Hybridoma Cell Lines

Hybridoma cells were grown in suspension culture in either serum-free medium (see Example 1) or in DMEM supplemented with 10% (v/v), heat inactivated foetal calf serum. Occasionally serum-free medium was supplemented with serum, as indicated in Table 4. Cells were cultured in either roller bottles or in shake-flasks, as in Example 1. Sodium butyrate was added to cultures immediately after inoculation.

Butyrate treatment increased the amount of antibody produced per cell. Table 4 shows increase in harvest antibody titre due to butyrate treatment, for a number of different hybridoma cell lines.

TABLE 4

| CELL LINE | CULTURE MEDIUM | ADDED BUTYRATE CONCENTRATION (mM) | HARVEST ANTIBODY TITRE (mg/liter) |
| --- | --- | --- | --- |
| A | SFM | 0.00 | 28 |
|   |     | 0.35 | 35 |
|   |     | 0.50 | 36 |
| B | SFM + 10% FCS | 0.00 | 173 |
|   |               | 0.35 | 232 |
|   |               | 0.50 | 240 |
| C | DMEM +10% FCS | 0.00 | 51 |
|   |               | 0.50 | 71 |
| D | SFM + 10% FCS | 0.00 | 29 |
|   |               | 0.35 | 39 |
|   |               | 0.50 | 50 |
| E | SFM | 0.00 | 46 |
|   |     | 0.35 | 56 |
|   |     | 0.50 | 86 |
| F | SFM + 5% FCS | 0.00 | 90 |
|   |              | 0.50 | 132 |
| G | SFM | 0.00 | 10 |
|   |     | 0.25 | 11 |
|   |     | 0.50 | 13 |
| H | SFM | 0.00 | 62 |
|   |     | 0.50 | 109 |
| I | DMEM + 5% FCS | 0.00 | 113 |
|   |               | 0.35 | 135 |
|   |               | 0.50 | 154 |
| J | DMEM + 10% FCS | 0.00 | 32 |
|   |                | 0.50 | 54 |
|   |                | 0.75 | 55 |
| J | SFM | 0.00 | 37 |
|   |     | 0.50 | 72 |
|   |     | 1.00 | 102 |
| K | SFM + 1% FCS | 0.00 | 15 |
|   |              | 0.50 | 26 |
| L | SFM | 0.00 | 34 |
|   |     | 0.25 | 50 |
|   |     | 0.50 | 58 |

SFM = SERUM-FREE MEDIUM

EXAMPLE 6

Effect of Varying Alkanoates and Antibody Production From Hybridoma Cells

NB1/19 cells were cultured as in Example 1. Varying straight chain sodium alkanoate salts (propionate, butyrate, pentanoate or hexanoate) were added to the inoculum at the concentrations indicated in Table 5.

Table 5 shows that treatment with alkanoate salts gives increased productivity from hybridoma cells.

TABLE 5

| ALKANOATE | CONCENTRATION OF ALKANOATE (mM) | PRODUCTIVITY (ug antibody per 10$^5$ cells) | | RELATIVE PRODUCTIVITY (1% OF CONTROL) | | AVERAGE DATA FROM EXP. #1 & #2 |
| --- | --- | --- | --- | --- | --- | --- |
|     |     | EXP. #1 | EXP #2 | EXP. #1 | EXP. #2 | #2 |
| CONTROL | 0.00 | 3.30 | 2.39 | 100.00 | 100.00 | 100.00 |
| PROPIONATE | 0.59 | 5.70 | ND | 172.7 | ND | 172.73 |
|            | 1.00 | 7.03 | 4.95 | 213.0 | 207.1 | 210.07 |

TABLE 5-continued

| ALKANOATE | CONCENTRATION OF ALKANOATE (mM) | PRODUCTIVITY (ug antibody per $10^5$ cells) EXP. #1 | EXP #2 | RELATIVE PRODUCTIVITY (1% OF CONTROL) EXP. #1 | EXP. #2 | AVERAGE DATA FROM EXP. #1 & #2 |
|---|---|---|---|---|---|---|
| BUTYRATE | 0.50 | 7.00 | 4.7 | 212.1 | 196.7 | 204.39 |
|  | 1.00 | ND | 8.80 | ND | 368.2 | 368.20 |
| PENANOATE | 0.50 | 5.40 | ND | 163.6 | ND | 163.64 |
|  | 1.00 | 6.80 | 5.50 | 206.1 | 230.1 | 230.1218.09 |
| HEXANOATE | 1.00 | 3.70 | 2.30 | 112.1 | 96.2 | 104.18 |
|  | 1.50 | 4.50 | ND | ND | 136.4 | ND 136.36 |
|  | 5.00 | ND | 5.30 | ND | 221.8 | 110.88 |

ND = not done
EXP. = Experiment

EXAMPLE 7

Butyrate Treatment Increases Production of Recombinant tPA From a Cell Line

A mouse C127 cell line producing recombinant tissue plasminogen activator (tPA) was cultured on microcarriers (gelibeads, K.C. Biologicals) in spinner vessels (Bellco). The growth medium was DMEM supplemented with 10% foetal calf serum. The concentration of microcarriers were 5 grams (dryweight) per liter of medium. Cells were inoculated at a density of $1 \times 10^5$ cells per ml.

After the cells had grown to confluency on the surface of the microcarriers, growth medium was aspirated and replaced with a protein-free DMEM-based maintenance medium containing the butyrate. Control cultures received no butyrate. Maintenance medium was replaced with fresh maintenance medium (containing butyrate) at the times shown in Table 6.

Cell density was determined by counting nuclei which were released from cells by hypotonic lysis (ref. Absher, in "Tissue Culture Methods and Applications", Kruse & Patterson, Academic Press 1973). The concentration of tPA in the supernatant was assayed using the fibrin-agar method.

TABLE 6

| MAINTENANCE PERIOD (hours) |  | CONCENTRATION OF BUTYRATE | | | |
|---|---|---|---|---|---|
|  |  | 0 | 0.5 mM | 1.0 mM | 2.5 mM |
| 46 | CELL DENSITY ($\times 10^5$ cells/ml) | 10.8 | 11.1 | 11.5 | 9.6 |
|  | CONCEN-TRATION OF TPA PER ML (arbitrary units) | 100 | 159 | 191 | 945 |
| 92 | CELL DENSITY ($\times 10^5$ cells/ml) | 13.7 | 10.3 | 9.2 | 7.6 |
|  | CONCEN-TRATION OF TPA PER ML (arbitrary inits) | 100 | 143 | 157 | 1782 |
| 140 | CELL DENSITY ($\times 10^5$ cells/ml) | 19.1 | 12.3 | 19.4 | 6.6 |
|  | CONCEN-TRATION OF TPA PER ML (arbitrary units) | 100 | 186 | 236 | 3468 |

I claim:

1. A process for the production of a protein, comprising the steps of:

culturing genetically manipulated cells excluding hybridomas which constitutively produce the protein in the presence of an alkanoic acid or salt thereof, the alkanoic acid or salt thereof present at a concentration at which production of the protein is enhanced compared to the production of the protein in the absence of the alkanoic acid or salt thereof but at which concentration the cell growth rate is not decreased;

continuing said culturing until the protein accumulates; and isolating the protein.

2. A process according to claim 1, wherein the alkanoic acid or salt thereof which enhances protein production is butyric acid or a salt thereof.

3. A process according to claim 2, wherein the alkanoic acid or salt thereof which enhances protein production is sodium butyrate.

4. A process according to claim 1, wherein the alkanoic acid or salt thereof is present at a concentration of from about 0.1 mM to about 10 mM.

5. A process according to claim 4, wherein the alkanoic acid or salt thereof is present at a concentration from about 0.3 mM to about 2.5 mM.

6. A process according to claim 1, wherein the alkanoic acid or salt thereof is selected from the group consisting of propionic, pentanoic and hexanoic acids or salts thereof.

7. A process according to claim 6, wherein the concentration of the alkanoic acid or salt thereof is from about 0.1 mM to about 5.0 mM.

8. In a method of obtaining a protein by cell culture comprising the steps of:

(a) culturing genetically modified cells excluding hybridomas which produce the protein;

(b) continuing said culturing step until the protein accumulates; and (c) isolating the protein;

the improvement comprising carrying out said culturing step in the continuous presence of an alkanoic acid or salt thereof in a concentration of between about 0.1 mM and about 10 mM which production of the protein is enhanced compared to production of the protein in the absence of said alkanoic acid or salt thereof.

* * * * *

UNITED STATES PATENT AND TRADEMARK OFFICE
CERTIFICATE OF CORRECTION

PATENT NO. : 6,228,618 B1        Page 1 of 1
DATED     : May 8, 2001
INVENTOR(S) : Raymond P. Field It is certified that error appears in the above-identified patent and that said Letters Patent is hereby corrected as shown below:

Title page,
Item [54] the title should read, -- PRODUCTION OF PROTEINS BY CELL CULTURE --

Signed and Sealed this

Thirteenth Day of November, 2001

Attest:

*Attesting Officer*

NICHOLAS P. GODICI
*Acting Director of the United States Patent and Trademark Office*